United States Patent [19]

Fisher et al.

[11] Patent Number: 5,673,703
[45] Date of Patent: Oct. 7, 1997

[54] APPARATUS FOR AUTOMATED DETERMINATION OF LOW FREQUENCY TACTILE THRESHOLDS

[75] Inventors: John H. Fisher; Barry L. Evans; Kenneth W. Horch, all of Salt Lake City, Utah

[73] Assignee: Ztech, L.C., Salt Lake City, Utah

[21] Appl. No.: 390,739

[22] Filed: Feb. 17, 1995

[51] Int. Cl.⁶ .................................................... A61B 5/00
[52] U.S. Cl. .................................... 128/739; 128/744
[58] Field of Search ................................ 128/739, 740, 128/744

[56] References Cited

U.S. PATENT DOCUMENTS

| | | | |
|---|---|---|---|
| 4,467,815 | 8/1984 | O'Brien et al. | 128/740 |
| 4,763,666 | 8/1988 | Strian et al. | 128/742 |
| 5,022,407 | 6/1991 | Horch et al. | 128/739 |
| 5,381,805 | 1/1995 | Tuckett et al. | 128/744 |

OTHER PUBLICATIONS

Chubbuck, J.G., "Small–motion Biological Stimulator," Appl. Phys. Lab. Tech. Digest, May–Jun. 1966, pp. 18–23, 1966.

Conomy, J.P. and K.L. Barnes, "Quantitative Assessment of Cutaneous Sensory Function in Subjects with Neurologic Disease," J. Neurolog. Sci., vol. 30, pp. 221–235, 1976.

Dyck et al. "Clinical vs Quantitative Evaluation of Cutaneous Sensation," Arch. Neurol. vol. 33, pp. 651–655, 1976.

Dyck, P.J., P. W. Schultz, and P.C. O'Brien, "Quantitation of Touch–Pressure Sensation," Arch. Neurol., vol. 26, pp. 465–473, 1972.

Dyck, P.J., I.R. Zimmerman, P.C. O'Brien, A. Ness, P. Caskey, J. Karnes and W. Bushek, "Introduction of Automated Systems to Evaluate Touch–Pressure, Vibration, and Terhmal Cutaneous Sensation in Man," Ann. Neurol. vol. 4, No. 6, pp. 502–510, 1978.

Horch, K. M. Hardy, S. Jimenez, and M. Jabaley, "An Automated Tactile Tester for evaluation of cutaneous sensibility," J. Hand Surgery, vol. 17A, No. 5, pp. 829–837, 1992.

Advertising material from NK Biotechnical Engineering Co. describing NK Hand Assessment System. 1988.

Primary Examiner—Max Hindenburg
Attorney, Agent, or Firm—Eleanor V. Goodall

[57] ABSTRACT

An apparatus for automated testing of vibrotactile responses of a patient is disclosed. The embodiment of the invention comprises a component to apply indentations and vibrations to the patient's skin to test the patient's response to vibrotactile stimuli. In the preferred embodiment of the invention, a general purpose computer functions to control the operation of the system and to record and store the patient's responses. Indentations and vibrations are produced by off-axis rotational movement of a stimulation probe. A frequency modulated signal generated by the computer is used to control the motor which drives the stimulation probe. The embodiment of the present invention is able to reliably repeat each test so that the tests are reproducible and are carried out in an objective manner.

20 Claims, 6 Drawing Sheets

Microfiche Appendix Included
(1 Microfiche, 51 Pages)

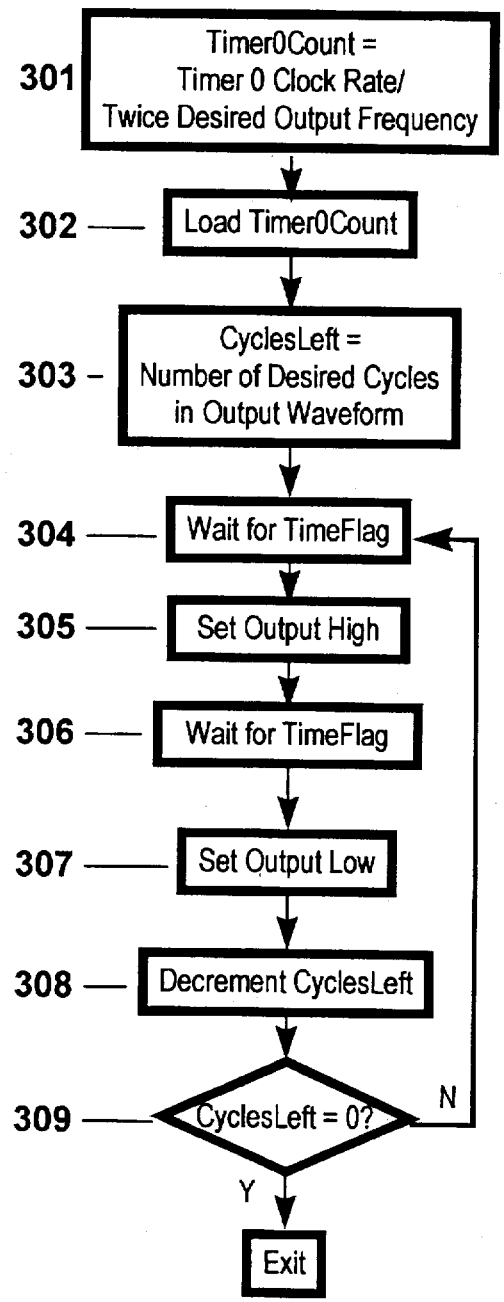
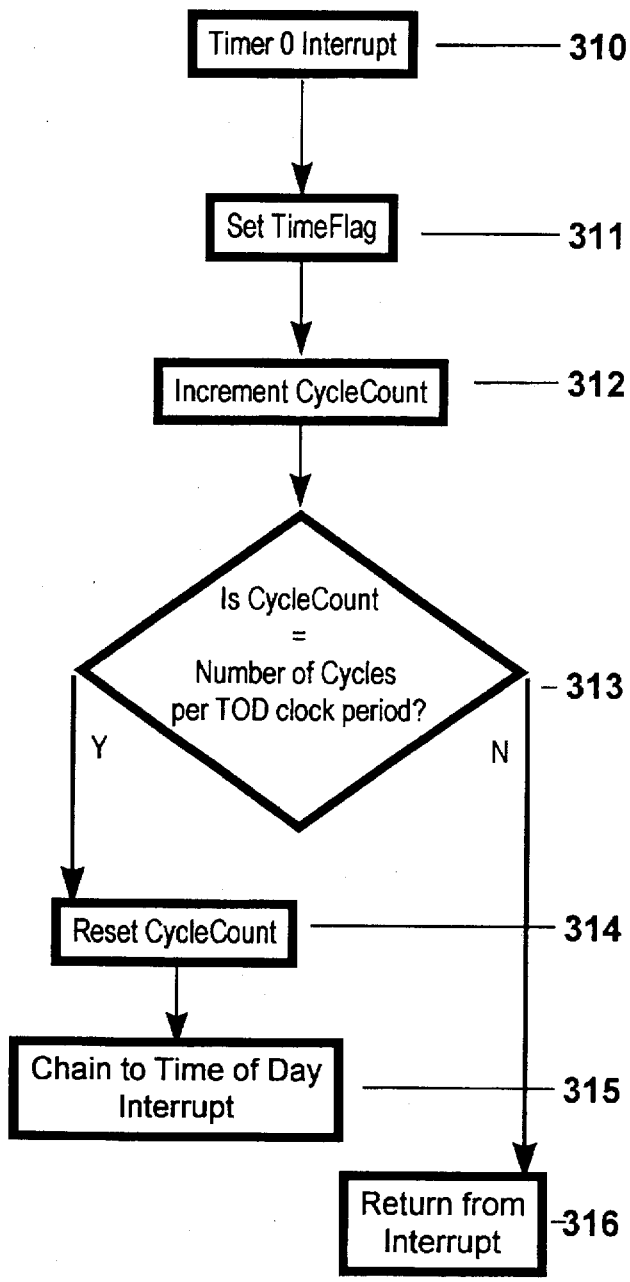
FIG. 3A
FIG. 3B

APPARATUS FOR AUTOMATED DETERMINATION OF LOW FREQUENCY TACTILE THRESHOLDS

I. BACKGROUND OF THE INVENTION

A. Field of the Invention

This invention relates to an apparatus used to determine the response of a human patient to vibrotactile stimulation. More particularly, the present invention relates to systems and methods for quantitatively determining a patient's responses to indentation and vibratory stimuli in a repeatable and reproducible manner.

Many medical professionals and researchers need to determine a patient's response to various modes of tactile stimulation. For example, medical professionals dealing with the human nervous system often need to determine a patient's response to various tactile stimuli to assess the extent of any damage to the nervous system due to trauma or a degenerative condition, and rehabilitation and physical therapists concerned with monitoring a patient's progress during recovery from a head injury, stroke, or some other event affecting somatosensory function also must conduct tactile testing. Moreover, primary care providers and paramedical personnel often desire to perform tactile testing as a routine screening procedure for their patients. Therefore, it is desirable that an inexpensive, automated system be available which allows stimuli to be delivered accurately and repeatably, and test results to be collected and stored.

B. The Background Art

The earliest prior art methods of testing the patient's response to vibration or skin indentation typically involve manually applying the stimulus to the patient. For example, tuning forks are used to determine the patient's tactile threshold of sensing vibration. Such methods involve a subjective determination by the administering technician and are not consistently applied or reproducible from test to test.

More recently, various mechanical stimulators have been developed which allow stimuli to be delivered in a more controlled and reproducible manner. For example, Chubbuck (APL Tech. Digest, May–June 1966, pp. 18–23, which is hereby incorporated by reference) developed an electromagnetic coil stimulator that utilizes a variable capacitance pickoff to provide feedback control of the displacement. Other commonly used transducers are galvanometers or electromagnetic drivers from commercial loudspeakers. These all have the advantage that they can be regulated by a voltage control signal. A disadvantage of many of the prior art devices is that they must be operated by someone with technical expertise. Ease of operation has been improved by the development of computer-controlled stimulation systems.

Stimulators which can be controlled by a voltage signal have been incorporated into computer-controlled devices for delivering stimuli and recording patient responses. At least one system for testing vibrotactile response is commercially available (Bruel and Kjaer Vibrometry System Type 9627, which is hereby incorporated by reference). Other systems for testing tactile response have been described in the literature (Dyck et al., Arch. Neurol., vol. 26, pp. 465–573, 1972; Dyck et al., Arch. Neurol., vol. 33, pp. 651–655, 1976; Dyck et al., Ann. Neurol. vol. 4, pp. 502–510, 1978; each of which is hereby incorporated by reference) or patented (Horch et al., U.S. Pat. No. 5,022,407, also incorporated by reference). In these systems, a computer program controls the production of an analog voltage signal for driving the stimulator. This signal is typically sent out via a digital-to-analog converter which is on a special-purpose card (D/A board) installed in the computer. Therefore, a standard personal computer must be modified by the installation of an D/A board if it is to be used in such a system, thus requiring additional effort and expense and precluding the use of most laptop computers. These systems utilize stimulation probes driven by relatively complex mechanical linkages, which limit the precision of the stimuli delivered and which have high parts and assembly costs.

In view of the foregoing, it would be an advance in the art to provide a system for performing automated tactile testing which could use a standard personal computer without modification. It would also be an advance in the art to provide such a system which utilized a simple mechanical system for driving the stimulation probe. It would be a further advance in the art to provide such a system inexpensively.

II. BRIEF SUMMARY AND OBJECTS OF THE INVENTION

The primary objectives of the present invention are:

1) to provide a system and method to accurately and reproducibly determine a patient's threshold to vibrotactile stimuli at a low cost;

2) to provide a system for determining vibrotactile threshold which does not require special expertise to operate;

3) to provide a system and method for automatically testing the vibrotactile responses of a patient which imposes quantitatively accurate stimuli upon command;

4) to provide a system for automatically determining the vibrotactile threshold of a patient which utilizes a standard personal computer without the need for installing a D/A or other interface board, thus reducing labor and expense;

5) to provide a system for automatically determining the vibrotactile threshold of a patient which utilizes a simple mechanical linkage to drive a stimulation probe, thereby reducing expense and improving accuracy of stimulation; and 6) to provide a system for automatically determining the vibrotactile threshold of a patient which maintains a record of the results of the testing.

In order to accomplish these and other objects, the preferred embodiment of the present invention includes a stimulation probe for application of steady and vibratory indentation of a patient's skin and a control apparatus to operate the tactile stimulation probe and record the responses of the subject. The preferred embodiment of the present invention automatically tests the sensation of cutaneous touch and vibration and provides for precise control of stimulus waveform so that reliable, quantitative data is obtained from the testing. The preferred embodiment of the present invention is able to repeatedly reproduce each test waveform from a consistent initial condition and uses appropriate sequences of stimuli so that the tests carried out are reproducible and accomplished in a minimum of time.

The cost of the system is minimized by using a frequency modulated signal generated by a personal computer and transmitted through one of its standard communications ports to control the stimulation apparatus, avoiding the need for acquisition and installation of special hardware in the personal computer. Further cost savings and improved reliability and accuracy of the device are obtained by mounting the stimulating probe on an arm or plate attached directly to the shaft of the galvanometer or pen chart motor, avoiding parts and assembly costs of more elaborate linkages and, more importantly, the imprecision they impose.

The use of a preprogrammed computer as part of the control apparatus minimizes the need for technical expertise on the part of the operating technicians and maximizes the present invention's flexibility by allowing new stimulus paradigms to be incorporated into the testing protocol by altering the programming code of the computer. Appropriate programming can be accomplished in software, firmware (ROM), microcode or at the hardware level.

The present invention could also perform diagnostic clinical tests for which manual methods are inadequate, such as determining threshold values for sensing changes in vibratory frequency. The present invention also has application in research settings where testing to determine responses to cutaneous vibrotactile stimuli are important, such as in the study of peripheral nerve regeneration.

III. BRIEF DESCRIPTION OF THE DRAWINGS

FIG. 3A is a flowchart diagram showing the logic used in the generation of a frequency modulated signal on a communication port of a microcomputer in the preferred embodiment of the invention.

FIG. 3B is a flowchart diagram showing the operation of an interrupt handling routine used to handle interrupts generated by time-of-day timer in preferred embodiment of the invention.

IV. DETAILED DESCRIPTION OF THE PREFERRED EMBODIMENT

Figure 1:
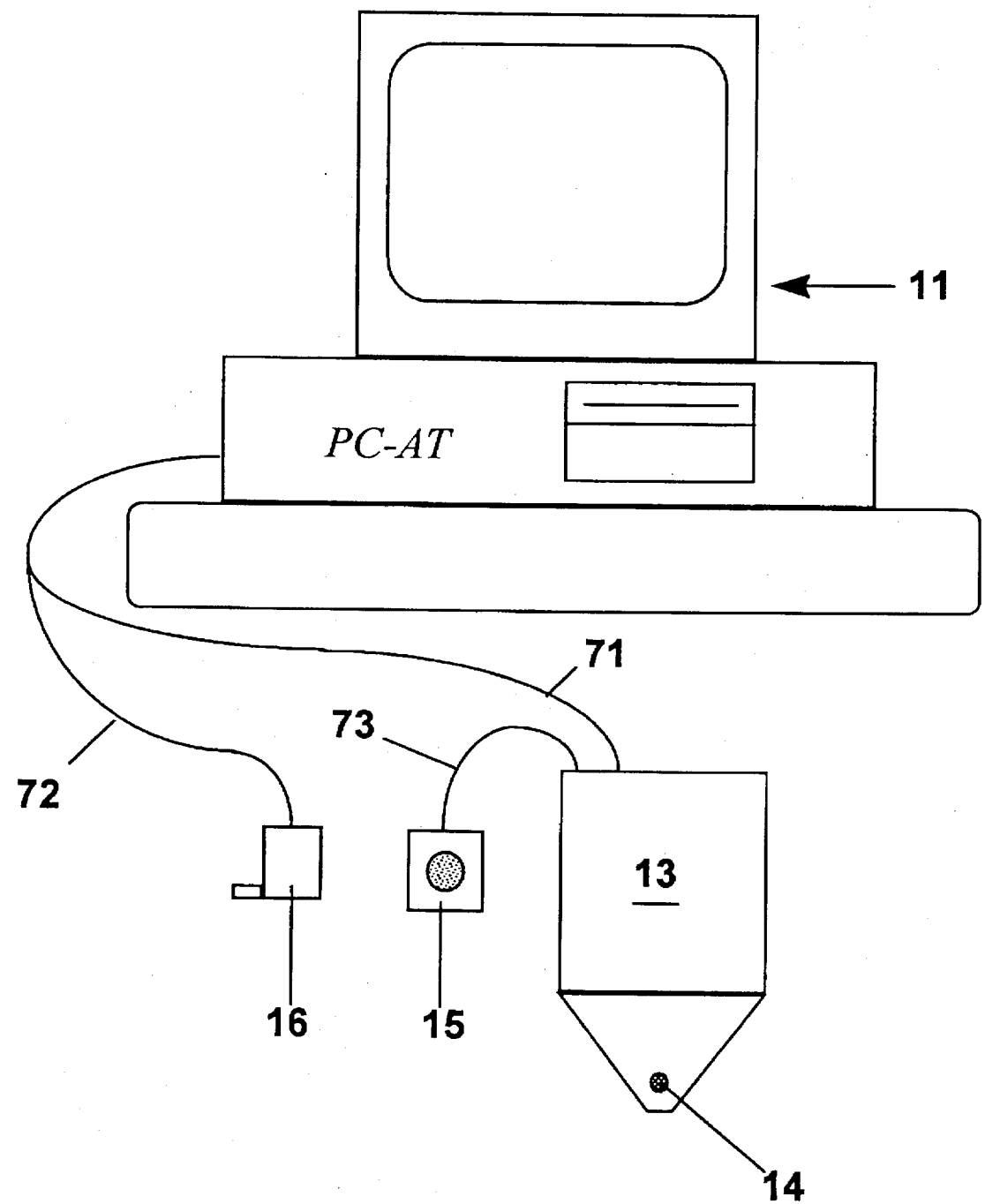
FIG. 1 is an overall view of the preferred embodiment of the invention.

Represented in FIG. 1 is the control apparatus, which in the preferred embodiment includes a microcomputer, generally designated as 11, which preferably is equivalent to an International Business Machines personal computer using an Intel 80286 or higher microprocessor or its equivalent and running the MSDOS operating system or its equivalent, or any other control apparatus having the capabilities to perform the functions described herein. The microcomputer 11 includes a standard serial or parallel communication port, time-of-day clock, display and keyboard.

Also shown in FIG. 1 is stimulation apparatus 13 which is connected to microcomputer 11 by a cable 71 from a serial or parallel port and contains the dedicated electronic circuitry necessary to operate the stimulation producing components also contained therein. Stimulation apparatus 13 has a power supply; a printed circuit board containing a frequency-to-voltage converter, waveform shaper and power amplifier, and buffered output from switch apparatus 15; and a galvanometer or pen recorder motor with a stimulation probe 14 driven by the output of said power amplifier. Power is provided to stimulation apparatus 13 by a commercially available 12 VAC wall plug transformer 16 (via cables 72 and 71).

The operation of the invention is controlled by a programming code which is run on microcomputer 11. An example of the presently preferred programming code is attached hereto as appendix A. The programming code controls operation of the system to perform the following functions:

1) Collect patient data.
2) Create files in which to store said patient data.
3) Present sample vibratory stimuli to the patient so that the approximate threshold for detection of stimuli may be estimated.
4) Present a test sequence of stimuli to the patient so that the threshold for detection of vibratory stimuli may be determined.
5) Store stimulus parameters and threshold data in patient data files.

The test sequence generated by the stimulator includes the following steps: A stimulus is presented. If the stimulus is not detected by the patient, the next stimulus is made larger. If the stimulus is detected, the next stimulus is made smaller in amplitude. This process is repeated until a specified number of reversals between detecting a sequence of stimuli and not detecting a sequence of stimuli has occurred.

Further information about the operation of the programming code can be gained by examining the sample code attached in Appendix A or running said code on an IBM PC compatible computer using the MSDOS, or equivalent, operating system.

Figure 2:
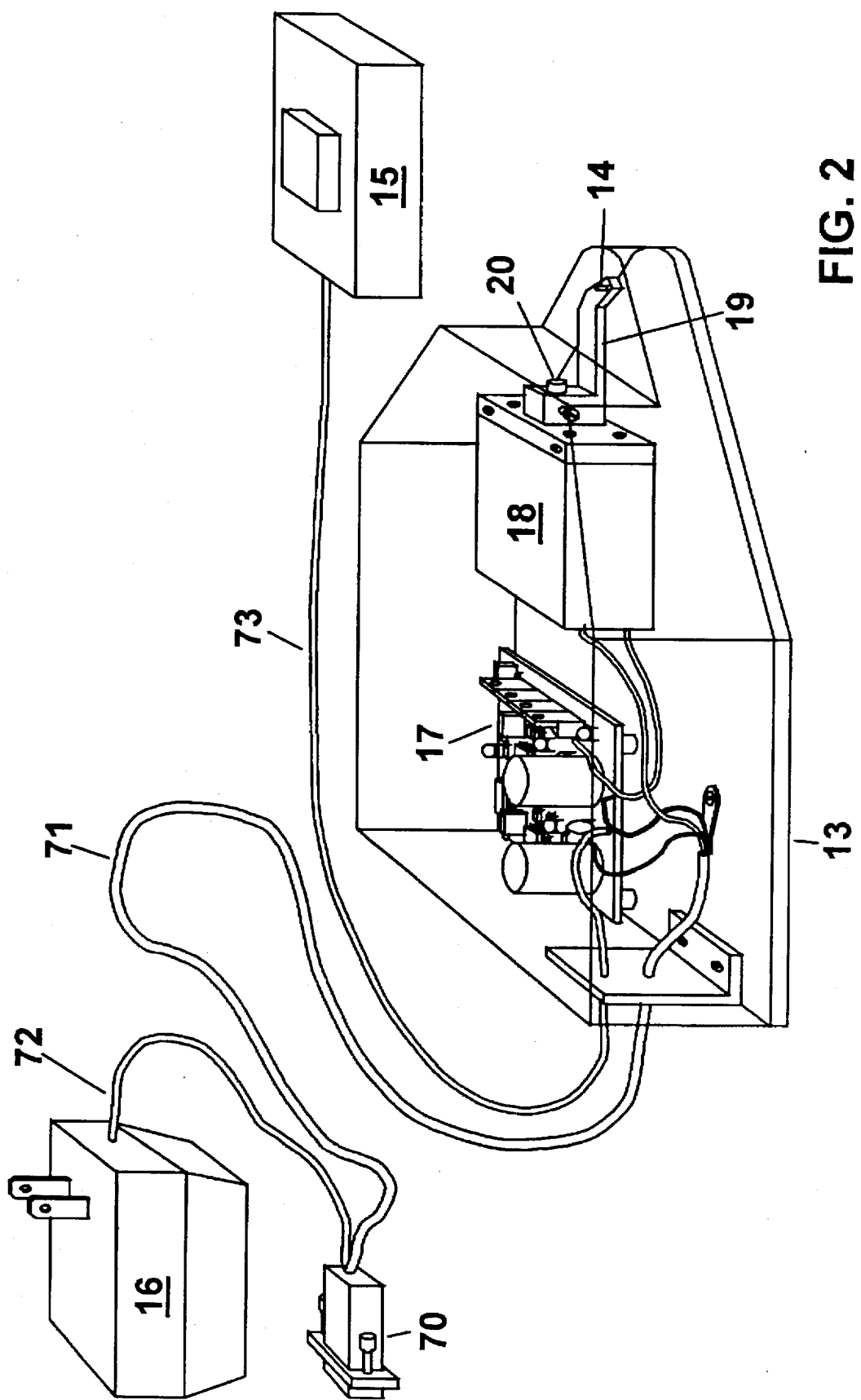
FIG. 2 is a partially cut away perspective view of the internal components of the stimulation apparatus and the attached switch apparatus and wall plug transformer.

FIG. 2 is a partially cut away perspective view of the stimulation apparatus 13. Also shown are power transformer 16 and switch apparatus 15. Switch apparatus 15 is connected to stimulation apparatus 13 by cable 73. Stimulation apparatus 13 is connected to microcomputer 11 via cable 71 and connector 70, and to power transformer 16 by cables 71 and 72. The apparatus includes a printed circuit board 17 and motor 18. In the preferred embodiment of the invention, said motor is a pen recorder motor. An example of a suitable recorder pen motor is model GM 12 from General Scanning Inc. Alternatively, said motor could be a galvanometer motor or other comparable motor. Motor 18 rotates shaft 20 which in turn moves a plate 19 on which is mounted a stimulation probe 14 which is used to deliver vibratory stimuli to the skin of the patient. In the preferred embodiment of the invention, stimulation probe 14 is a stainless steel, 1 mm diameter, blunt tipped probe. However, other probes may be used as well and are considered to fall within the scope of the present invention. Stimulation probe 14 is mounted on probe mount 19 (in this case a metal plate) which is attached to the galvanometer shaft 20 in such a way that its movement is centered in the horizontal plane. The tip of the stimulation probe is centered in a 2 mm diameter hole in the housing of the stimulation apparatus 13.

The vibratory stimuli delivered with stimulation probe 14 preferably consist of repetitive mechanical indentations of the skin. The amplitude and time course of displacement of the stimulation probe is determined by the frequency and temporal patterning of a series of pulses (logical 1's surrounded preceeded and followed by logical 0's) presented on one line of the computer's communication port (i.e. parallel or serial port). The programming code causes an appropriate pulse sequence to be generated on the basis of timing information available from the computer's internal time-of-day hardware. The microcomputer thus functions as a frequency generating apparatus. The internal time-of-day hardware comprises a timer chip (e.g. an 8254) having several timers on it, one of which (typically timer 0) regulates the time-of-day clock. During normal operation of the microcomputer, an interrupt is generated each time the count in the time-of-day timer (e.g. timer 0) reaches zero, and in response to said interrupt an interrupt handler updates the time-of-day clock. The programming code of the present invention reprograms the time-of-day timer to generate interrupts at a selected higher rate by loading a smaller than usual count into the timer. When a time-of-day interrupt is generated, a special-purpose interrupt handler which sends a frequency modulated signal to the parallel (or serial) port of the computer and also provides for the system clock to be updated after the appropriate number of interrupts has occurred is called.

The logic used in the preferred embodiment of the invention to generate a signal of a desired frequency on the computer's communication port is shown in FIG. 3A. FIG. 3B outline the routine used to handle interrupts generated by the time-of-day timer in the preferred embodiment of the invention.

Referring now to FIG. 3A, in step 301 the count to be loaded into the timer (e.g. time-of-day timer) is calculated from the timer clock rate and the desired output frequency. The timer count is calculated so that said timer will generate an interrupt at twice the desired output frequency. Because the computer output is toggled from high to low or low to high each time an interrupt occurs, the resulting output is a square wave at the desired frequency.

Said count is loaded into said timer in step 302. In step 303, a variable (e.g. "CyclesLeft") is set which indicates the number of cycles of the output waveform to be sent out on the computer's communication port. The program then waits for a flag ("TimeFlag") to be set (step 304). This is done by the interrupt handling routine each time an interrupt is generated by said timer. When said flag is set, the value on the computer communication port is set high (step 305). The program waits until said flag is again set (step 306) and then sets the value on the communication port low (step 307). The number of cycles remaining in the desired output signal is decremented in step 308. In step 309, it is determined whether the number of cycles remaining equals zero. If so, generation of the waveform at said desired output frequency is discontinued. Otherwise, the program returns to step 304 to wait for the next time said flag is set in order to continue waveform generation. If it is desired to generate a further waveform at a different output frequency, the logic depicted in FIG. 3A is re-entered at step 301, a new count value is calculated from the new desired output frequency, and said further waveform is generated. It will be appreciated by those of ordinary skill in the art that programming code can be written which utilizes the logic shown in FIG. 3A (or the equivalent) to generate an output waveform of varying frequency, by calculating a new count value and loading it into said timer each time it is desired to change the frequency of the output signal.

In the preferred embodiment of the invention, each time an interrupt is generated by the time-of-day timer, the interrupt handling routine represented in FIG. 3B is called (step 310). The flag ("TimeFlag") is then set (step 311). The setting of said flag is detected by the routine shown in FIG. 3A, as described previously. In step 312, a variable ("CycleCount") representing the number of timer cycles which have already occurred is incremented. In step 313, it is determined whether this variable is equal to the number of cycles in the time-of-day clock period. If so, said variable is reset (step 314) and the time-of-day interrupt handler routine, which updates the time-of-day clock is called (step 315). Otherwise, control returns from the interrupt handler routine to the main program (step 316). The output signal thus generated in the preferred embodiment of the invention is a square wave with a frequency half that of the counter/timer.

It will be appreciated by one of ordinary skill in the art that various functionally equivalent approaches may be taken, all of which utilize the basic principles of: setting one of the computer's internal counter/timers to generate a desired frequency, monitoring said counter/timer, and changing the value of one or more bits on a communication port from high to low or low to high to generate an output signal with frequency dependent on the counter/timer frequency.

In the preferred embodiment of the invention, the logic which controls output of the frequency modulated signal (shown in FIG. 3A) is separate from the interrupt handler routine which is called when an interrupt is generated by the time-of-day timer (shown in FIG. 3B). Alternatively, said logic could be incorporated into the interrupt handler logic.

The invention could also be varied by using some timer other than the time-of-day timer (i.e. timer 0 in a standard IBM-compatible microcomputer). For example, the timer typically used to control the speaker on a standard IBM-compatible microcomputer could be used (timer 2). Other timers may not generate interrepts as each cycle is completed; therefore it would be necessary to check the timer status from the software. Furthermore, although in the preferred embodiment of the invention, the timer counted down and the time that it reached zero was detected, a timer could also be programmed to count upward, and the maximum count could be detected. Any intermediate count could be detected to determine the completion of a timer cycle.

Although in the preferred embodiment of the invention the output port is toggled on each cycle of the counter/timer, giving rise to a squarewave output signal with a frequency half that of the counter/timer frequency, it would also be possible to generate an output signal with a frequency equal to the counter timer frequency, by toggling the output signal when the counter/timer has completed a cycle, and toggling it back to its starting value at some fixed delay (which could be controlled by software). It is not necessary that the high and low portions the output cycle are of equal durations. Nor is it necessary that the first part of the cycle is high and the second part low. Furthermore, the counter/timer frequency could be set to any integer multiple of the desired output frequency, such that an output cycle would be initiated every n counter/timer cycles, if the counter/timer frequency is n times the output frequency.

All of the modifications described herein are considered to fall within the scope of the invention. Furthermore, these examples are given to illustrate the operation of the invention, and it is considered that various other modifications which would be contemplated by those of ordinary skill in the art also fall within the scope of the invention.

In the preferred embodiment of the invention, the communication port on which said frequency modulated signal is sent is a standard serial port. Alternatively, said communication port could be a parallel port or some other port on the computer which has at least two bits which may be set independently and through which data may be sent and received. The frequency modulated signal is carried on one bit of said communication port, while a second bit is used to carry a signal from switch apparatus 15 which indicates detection of a stimulus. An electronic circuit which includes a frequency-to-voltage converter and accompanying amplifier circuitry located on printed circuit board 17 convert the former signal to a time varying (e.g., sinusoidal) signal that controls the rotation of the galvanometer shaft 20 which determines the extent to which the stimulation probe 14 projects through the hole in the housing of the stimulation apparatus. The system is able to provide a 200 μm indentation with sufficient force to compensate for the compliance of the skin over soft tissues but with minimal lateral displacement of the blunt tip, without the use of other mechanical linkages. In order to achieve this it is necessary that the housing of the stimulation apparatus be placed immediately over the probe mount 19 attached to the shaft of the galvanometer motor 18.

Figure 4B:
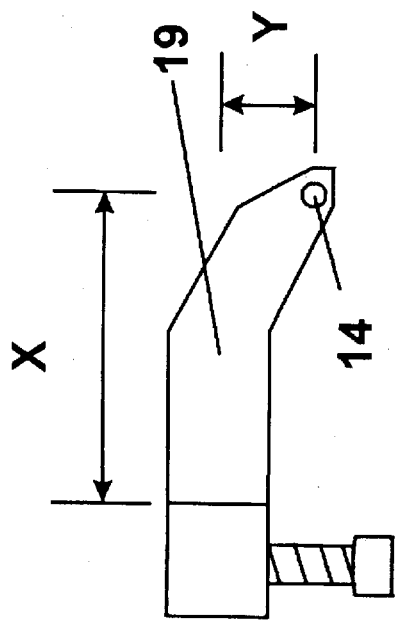
FIG. 4B is a detailed view of parts of the motor, probe mount and stimulation probe shown in top view.
Figure 4C:
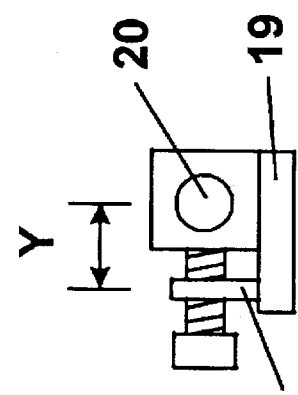
FIG. 4C is a detailed view of parts of the motor, probe mount and stimulation probe, shown in frontal view.
Figure 4A:
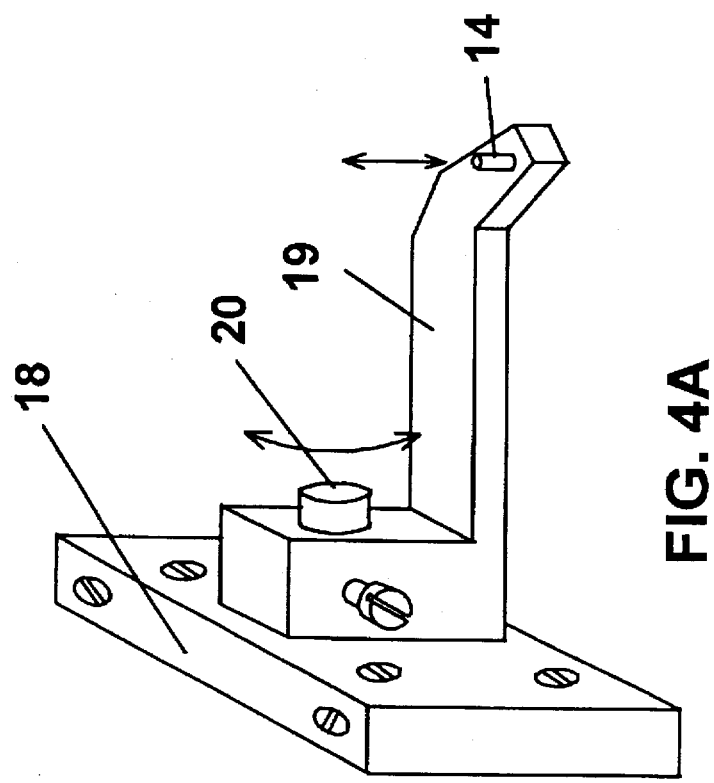
FIG. 4A is a detailed view of parts of the motor, probe mount and stimulation probe, shown in a perspective view.

Details of the stimulation probe 14, the probe mount 19 on which it is mounted, and its mode of operation are given in FIGS. 4A, 4B, and 4C. In FIG. 4A, the stimulation probe, probe mount and motor are shown in perspective. Probe mount 19 is preferably an aluminum plate shaped approximately as shown. Alternatively, other materials with comparable mechanical properties may also be used. Probe mount 19 can have various shapes, but the distance between the motor and the stimulation probe (indicated by X in FIG. 4B) is preferably no longer than about 80 mm. A longer distance will result in reduced accuracy of the indentation. FIG. 4C shows stimulation probe 14 in relation to shaft 20, from the front. The distance between the axis of rotation of shaft 20 and the path of stimulation probe 14 (indicated by Y in FIG. 4B and 4C) must be short enough that adequate force is delivered by the stimulation probe, and large enough that roughly linear movement of the stimulation probe tip is produced through its full range of motion. For example, if a General Scanning Model GM 12 motor is used, Y must be less than 100 mm to generate forces up to 0.15N, which would typically be the maximum force needed in tactile stimulation applications; if a probe displacement of 200 μm is desired, distance Y must be greater than 4 mm. In the preferred embodiment of the inventions shown here, distance X is between 30 and 60 mm and distance Y is between 4 and 20 mm. Although for testing vibrotactile response it is preferable to use a probe with a circular cross section and 1 mm diameter, the diameter and shape of the probe can be varied without departing from the essential nature of the invention. The length of the stimulation probe must be sufficient to be flush with the surface of the housing, such that it is level with the center of rotation of the shaft.

Figure 5A:
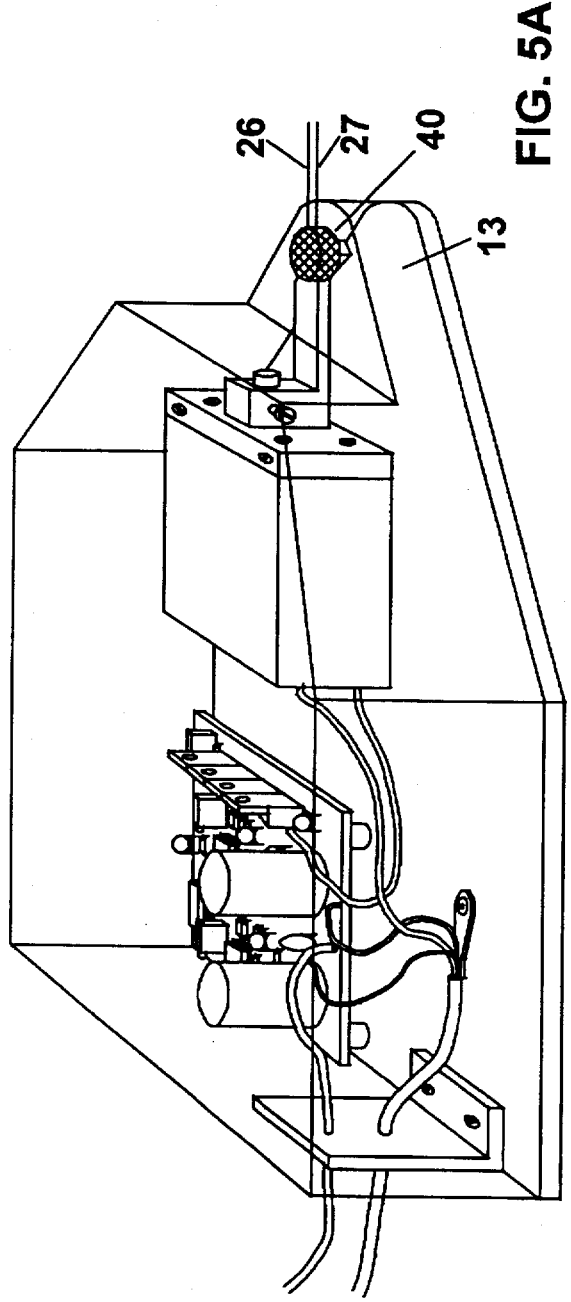
FIG. 5A is a perspective view of the calibration device in position over the stimulation probe.
Figure 5B:
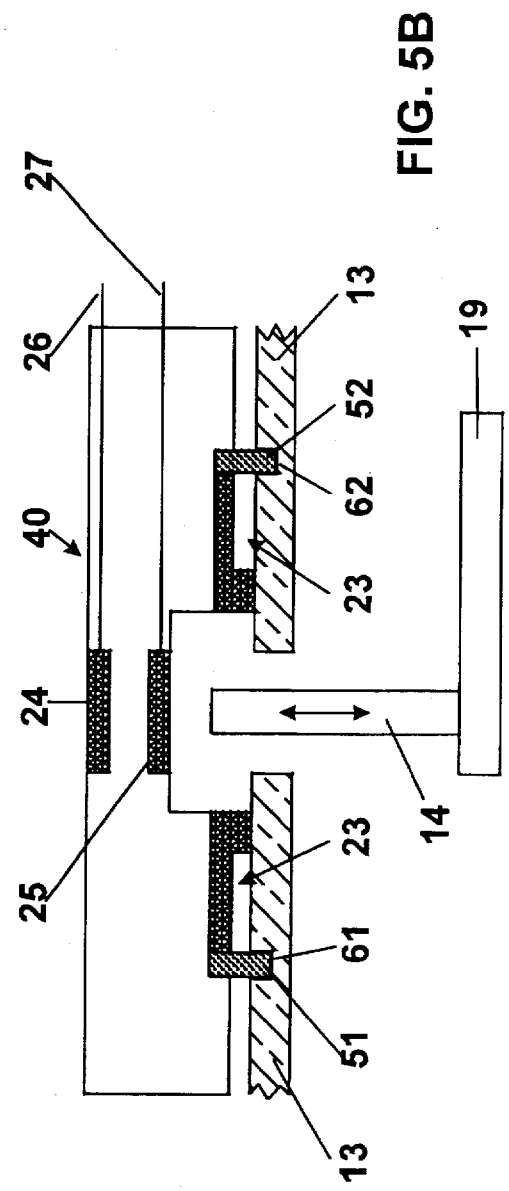
FIG. 5B is a cross sectional view of the calibration device in position over the stimulation probe.

The stimulator is calibrated with the use of a separate calibration device 40, which is placed over stimulation probe 14 of the stimulator, as shown perspectively in FIG. 5A and in cross section in FIG. 5B. Cap 21, made of a nonconductive material, is aligned over the stimulation probe 14 by pins 51 and 52 that fit into holes 61 and 62, respectively, in the housing of stimulation apparatus 13. Two pins and holes are used in the preferred embodiment of the invention; however, it will be appreciated by those skilled in the art that any other number of pins which provides for a stable attachment of calibration device 40 to stimulation apparatus 13 falls within the scope of the invention. The lower surface of cap 21 is lined with a conductive shield 23 that is tied to system electrical ground, as is stimulation probe 14, which is grounded through mounting plate 19. A high frequency (e.g., 50 kHz) voltage signal is applied to a first conductive plate 24 in the top of the calibrator cap through wire 26. A second conductive plate 25 on the surface of the cap opposite plate 24 forms two capacitive elements: a first with plate 24 and a second with the stimulation probe 14, forming a capacitive voltage divider. The output of this divider is carried on wire 27 to a measurement instrument (for example an oscilloscope). The signal is preferably amplified prior to measurement. During calibration, stimulation probe 14 is caused to vibrate at a specified amplitude by the computer control program, and said measurement instrument is used to measure changes in the amplitude of the applied, high frequency signal as seen at the lower plate 25 due to changes in capacitance between the stimulation probe 14 and the lower plate 25 during the sinusoidal oscillations of the stimulation probe. The measured signal is an amplitude modulated 50 kHz carrier, which is rendered largely immune to interfering noise by appropriate filtering in the amplifier system. Since the initial capacitance between the stimulation probe 14 and plate 25 can be measured (with, for example, a capacitance meter), the changes in capacitance during probe movement can be converted into displacement of the stimulation probe, providing a basis for calibration of the instrument.

Figure 6:
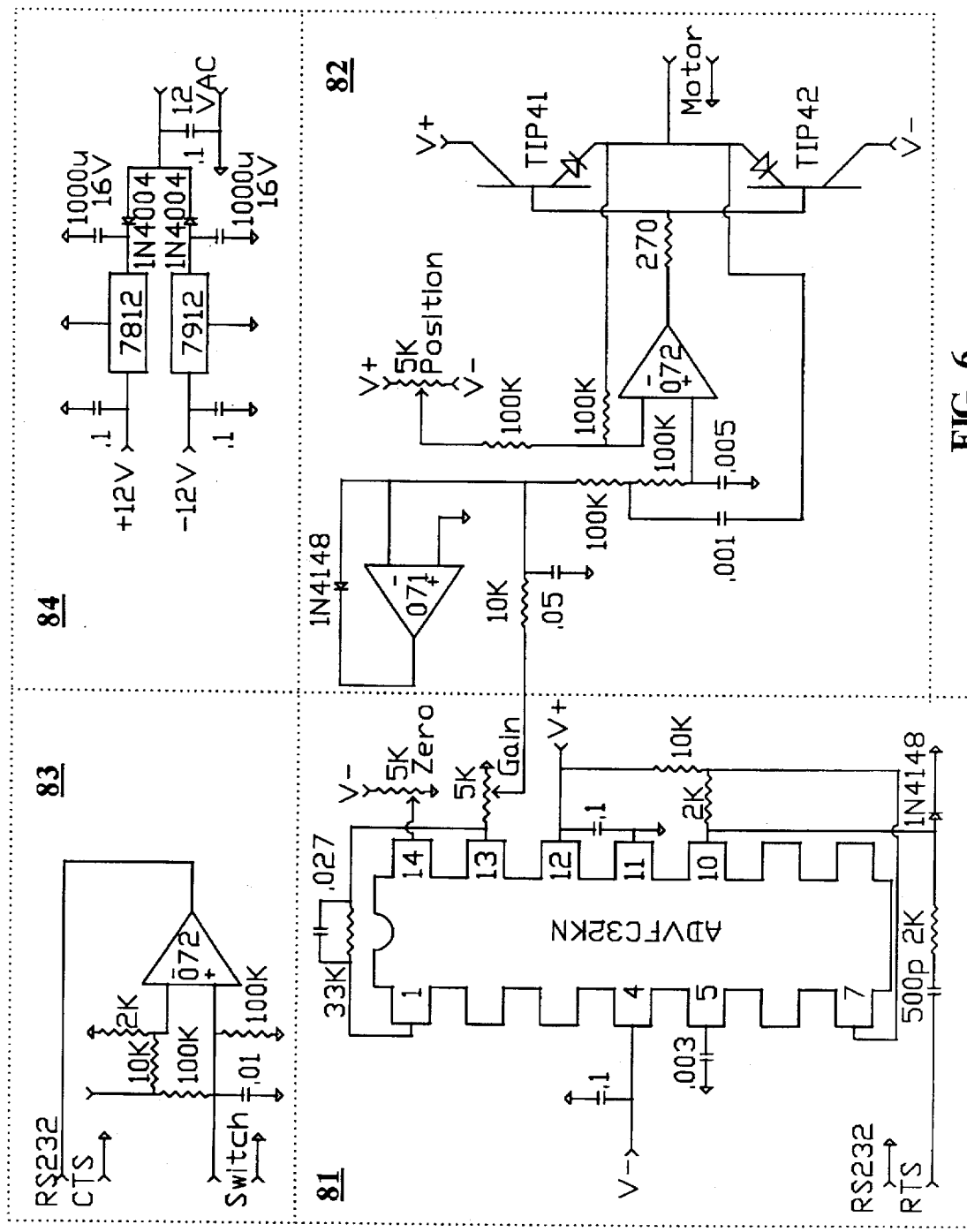
FIG. 6 is a schematic diagram of the electronic circuitry contained in the stimulation apparatus in the preferred embodiment of the invention.

FIG. 6 is an electrical schematic of the electronic circuit which is present on the circuit board in stimulation apparatus (as shown in FIG. 2). The circuit includes a frequency-to-voltage converter portion 81 (surrounded by dotted line). The control signal from the computer is sent to the freqency-to-voltage converter via a single bit of the computer serial (or parallel) port (labelled RS232 RTS). The frequency-to-voltage converter (an ADVFC32 in this instance, but any equivalent device or circuitry may alternatively by used) converts a frequency modulated pulse train from the computer port to an appropriate analog input voltage for the galvanometer driver amplifier 82 (opamp type 072 or equivalent and transistors TIP41 and TIP42 or equivalent are used). The output of galvanometer driver amplifier 82 is a DC voltage signal which is connected to the input of the galvanometer motor and causes the production of a rotation proportional to the amplitude of the signal. Also present on the circuit board is switch buffer (opamp comparator) circuit 83, which provides a logic 0 to the computer port if the switch in switch apparatus 15 is open or a logic 1 if it is closed (indicating detection of a stimulus); and transformer circuit 84 which converts the 12 VAC power line signal to a +12 or −12 VDC signal which is used to power the components on the circuit board. In the preferred embodiment of the invention, switch apparatus 15 includes a momentary contact switch which is connected to switch buffer circuit 83. Other switch/circuit combinations which provide equivalent switching function can be used in switch apparatus 15 and the selection of such a combination falls within the knowledge of one of ordinary skill in the art. The binary signal input to the computer port is detected by the computer (which is programmed to function in a signal detecting capacity), which generates additional stimuli or greater or lesser amplitude to form a test sequence, as described previously.

In use, the patient places his or her finger or other part to be tested over the stimulation probe 14, the operator instructs the patient on the basic procedure to be followed, and initiates the test. At the beginning of each test sequence the technician is presented with an option of choosing whether or not to store the results in a data file, what starting amplitude to use for the tests, and whether or not to give sample stimuli to the patient before the formal threshold testing is performed. Further operation of the inventive system is as described herein. The invention makes possible the testing of patient response to vibrotactile stimuli with minimum of equipment, expense and operator training.

The present invention is particularly adapted for use in clinical settings but may also be used in analytical or research applications. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An apparatus for automatically testing the vibrotactile sensory response of a patient, comprising:
   a) a stimulation apparatus for producing vibrotactile stimuli of precise predetermined amplitude and time course, the stimulation apparatus comprising:
      i) a motor which produces rotational motion of a shaft in response to a control signal;
      ii) a probe mount rigidly attached to said shaft; and
      iii) a stimulation probe rigidly attached to said probe mount at a distance from the axis of rotation of said shaft and with an orientation such that rotation of said shaft results in the movement of the stimulating surface of said stimulation probe about said axis at a fixed distance from said axis; and
   b) a control apparatus for controlling said stimulation apparatus, recording the patient's responses to cutaneous stimulation produced by said stimulation apparatus, and generating additional stimuli in response to the record of the patient's response to said stimuli.

2. An apparatus in accordance with claim 1 wherein said motor is a galvanometer motor; and wherein rotation of said shaft produces nearly linear movement of said stimulation surface over a range of at least 200 µm.

3. An apparatus in accordance with claim 1 wherein said motor is a pen recorder motor; and wherein rotation of said shaft produces nearly linear movement of said stimulation surface over a range of at least 200 µm.

4. An apparatus in accordance with claim 1 wherein said control apparatus comprises:
   i) a frequency generating apparatus for producing a frequency modulated digital signal;
wherein said stimulation apparatus further comprises:
   iv) an electronic circuit which converts said frequency modulated digital signal into an amplitude modulated analog control signal;
and wherein said amplitude modulated analog control signal controls rotational motion of said motor.

5. An apparatus in accordance with claim 1, further comprising:
   c) a switch apparatus which provides a signal to said control apparatus whereby said patient indicates detection of a vibrotactile stimulus.

6. An apparatus in accordance with claim 1, further comprising:
   c) a calibration device whereby the movement of said stimulation probe produced by a selected control signal may be measured and subsequently compared to the movement expected to be produced by said selected control signal.

7. An apparatus in accordance with claim 6, wherein said calibration device comprises:
   i) a cap of non-conductive material which is placed over said stimulation probe and fixed with respect to the housing of said stimulation apparatus in such a manner that said stimulation probe can be moved with respect to said housing and said calibration device without contacting said calibration device;
   ii) a first conductive plate affixed to said cap parallel to the stimulation surface of said stimulation probe;
   iii) a second conductive plate affixed to said cap parallel to the stimulation surface of said stimulation probe and positioned between said first conductive plate and said stimulation probe, separated from said first plate by a layer of said non-conductive cap material and separated from said stimulation surface of said stimulation probe by a distance which depends upon the position of said stimulation probe;
   iv) a first capacitive element formed by said first plate, said layer of non-conductive cap material, and said second plate;
   v) a second capacitive element formed by said second plate and said stimulation probe, wherein the capacitance of said second capacitive element varies with change in position of said stimulation probe; and
   vi) a capacitive voltage divider formed by said first and second capacitive elements;
wherein a change of position of said probe can be calculated from a change in potential dropped across said first capacitive element.

8. An apparatus in accordance with claim 4 wherein said electronic circuit comprises a frequency-to-voltage converter.

9. An apparatus in accordance with claim 4, wherein said control apparatus comprises a microcomputer having at least one serial port, and wherein said microcomputer is programmed to output said frequency modulated digital signal on said serial port.

10. An apparatus in accordance with claim 4, wherein said control apparatus comprises a microcomputer having at least one parallel port, and wherein said microcomputer is programmed to output said frequency modulated digital signal on said parallel port.

11. An apparatus for automatically testing the vibrotactile sensory response of a patient, the apparatus comprising:
   a) a stimulation apparatus for producing vibrotactile stimuli of precise predetermined amplitude and time course, comprising:
      i) a motor which produces rotational motion of a shaft in response to a control signal;
      ii) a probe mount rigidly attached to said shaft; and
      iii) a stimulation probe rigidly attached to said probe mount at a distance from the axis of rotation of said shaft and with an orientation such that rotation of said shaft results in the movement of the stimulating surface of said stimulation probe about said axis at a fixed distance from said axis;
   b) a frequency-generating computer for generating a frequency modulated digital signal;
   c) an electronic circuit for converting said frequency modulated digital signal to an amplitude modulated analog signal which is used as said control signal;
   d) a switch apparatus whereby the patient indicates detection of a vibrotactile stimulus, and from which a signal is produced which indicates that said detection has occurred; and
   e) a signal-detecting computer for detecting signals from said switch apparatus and generating additional stimuli in response to detection of signal from said switch apparatus.

12. An apparatus in accordance with claim 11 wherein said motor is a galvanometer motor.

13. An apparatus in accordance with claim 11 wherein said motor is a pen recorder motor.

14. An apparatus in accordance with claim 11 wherein said electronic circuit comprises a frequency-to-voltage converter.

15. An apparatus in accordance with claim 11, wherein a microcomputer serves as both said signal-generating computer and said signal-detecting computer.

16. An apparatus in accordance with claim 11, further comprising a calibration device whereby the movement of said stimulation probe produced by a selected control signal may be measured and subsequently compared to the movement expected to be produced by said selected control signal.

17. An apparatus in accordance with claim 15, wherein said microcomputer has at least one counter/timer and at least one communication port, and wherein said frequency modulated digital signal is generated by the steps:

a) loading a count into the counter/timer of microcomputer, said count being selected so that the frequency at which said counter/timer cycles is n times the desired frequency of said frequency modulated digital signal, wherein n is an integer;

b) detecting completion of a cycle by said counter/timer;

c) toggling the value of at least one bit in the communication port of said microcomputer;

d) after a delay, toggling the value of said at least one bit in said communication port of said microcomputer;

e) repeating steps b) through d) every n cycles of said counter/timer for as long as it is desired to produce pulses at said desired frequency;

f) repeating step a), followed by steps b) through e) whenever it is desired to change the frequency of said frequency modulated digital signal.

18. An apparatus in accordance with claim 15 wherein said microcomputer has at least one serial port, and wherein said microcomputer is programmed to output said frequency modulated digital signal on said serial port.

19. An apparatus in accordance with claim 15, wherein said microcomputer has at least one parallel port, and wherein said microcomputer is programmed to output said frequency modulated digital signal on said parallel port.

20. An apparatus in accordance with claim 17, wherein said counter/timer is a time-of-day counter; wherein completion of each cycle by said counter/timer is accompanied by the generation of an interrupt; wherein said interrupt causes an interrupt-handling routine to be run in which a flag is set to indicate the occurrence of said interrupt; and wherein completion of said each cycle is detected by monitoring the status of said flag.

* * * * *